United States Patent [19]
Gillis et al.

[11] Patent Number: 5,202,118
[45] Date of Patent: Apr. 13, 1993

[54] METHOD FOR PROMOTING WOUND HEALING USING IL-1

[75] Inventors: Steven Gillis, Mercer Island; Cindy A. Jacobs, Seattle, both of Wash.

[73] Assignee: Immunex Corporation, Seattle, Wash.

[21] Appl. No.: 695,860

[22] Filed: May 6, 1991

Related U.S. Application Data

[63] Continuation-in-part of Ser. No. 650,380, Feb. 4, 1991, abandoned, which is a continuation-in-part of Ser. No. 134,680, Dec. 18, 1987, abandoned.

[51] Int. Cl.$^5$ ............................................. A61K 37/02
[52] U.S. Cl. .................................. 424/85.2; 424/85.1; 514/2; 514/8; 514/21; 514/886; 530/351
[58] Field of Search ........................... 424/85.1, 85.2; 514/2.8, 21, 886; 530/351

[56] References Cited

U.S. PATENT DOCUMENTS 5,035,887 7/1991 Antoniades et al. ................ 530/35.1

OTHER PUBLICATIONS

Arai et al, *Annu Rev Biochem*, 1990, 54, pp. 783–793.
Dijki et al, *Bio/Technol* vol. 7, 1989, pp. 793–798.
Foret et al, *Arch Surg* 124, 1989, pp. 1422–1428.
Bell et al, *J Cellular Biochem*, suppl 15F, 1991, p. 201.
Broadley et al, *J Cellular Biochem*, Suppl 15F, 1991, p. 162 (#Q022).
Zeck-Kapp et al, *Imminobiol* 179(1) 1989, pp. 44–55 (abstract only).
Zeck-Kapp et al, *J Invest Deamatal*, 95(6), 1990, pp. 94S–99S (abst. only).
Carrico et al. "Biology of Wound Healing" *Surgical Clinics of North America*, 64:721–733 (1984).

Primary Examiner—Garnette D. Draper
Attorney, Agent, or Firm—Scott G. Hallquist; Christopher L. Wight; Jeffery B. Oster

[57] ABSTRACT

Wound healing compositions comprising IL-1α and IL-1β proteins in a physiologically acceptable hydrophilic vehicle are used to promote wound healing.

8 Claims, 5 Drawing Sheets

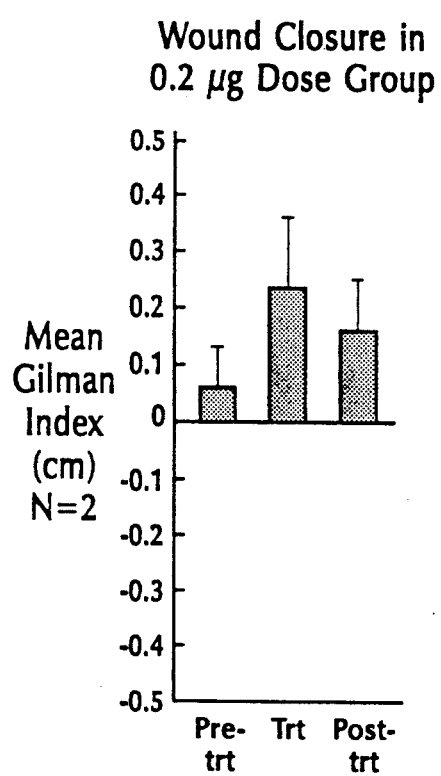
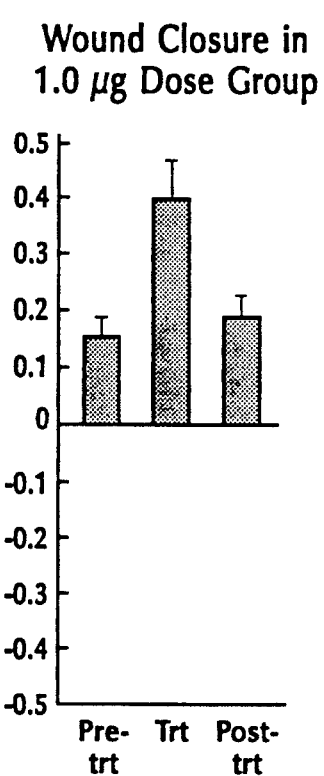
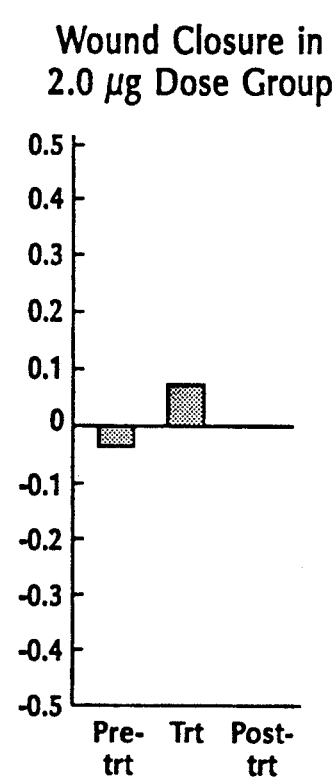
Figure 10
Figure 11
Figure 12

METHOD FOR PROMOTING WOUND HEALING USING IL-1

REFERENCE TO RELATED APPLICATIONS

This application is a continuation-in-part of U.S. patent application Ser. No. 07/650,380, filed Feb. 4, 1991, now abandoned which is a continuation-in-part of U.S. patent application Ser. No. 134,680, filed Dec. 18, 1987, now abandoned.

BACKGROUND OF THE INVENTION

The present invention provides topical therapeutic compositions for accelerating wound healing comprising mammalian IL-1 proteins.

Interleukin-1 (IL-1) refers to a family of polypeptides which are secreted by macrophages and certain other cell types in response to immunogenic and traumatic stimulation. IL-1 proteins have been associated with a complex spectrum of biological activities, and appear to play a primary role in initiating host response to injury and infection. IL-1 is a primary immunostimulatory signal capable of inducing thymocyte proliferation via induction of interleukin-2 release, and stimulating proliferation and maturation of B lymphocytes. In addition, IL-1 has been linked with prostaglandin production, inflammation, and induction of fever.

A review of the literature relating to IL-1 by Oppenheim et al., *Immunol. Today* 7: 45 (1986), reported that "IL-1 has multiple effects on cells involved in inflammation and wound healing." As shown by the disclosures of the following references, IL-1 is known to stimulate proliferation of fibroblasts and attract cells involved in the inflammatory response.

Postlethwaite et al., *J. Exp. Med.* 155: 801 (1983) described experiments which indicated that IL-1-like molecules were capable of stimulating fibroblast proliferation in vitro and also the release of collagenase by cultured fibroblasts.

Luger et al., *J. Immunol.* 131: 816 (1983), Sauder et al., *J. Immunol.* 132: 828 (1984), and several papers appearing in Kluger et al., eds., *The Physiologic, Metabolic, and Immunologic Actions of Interleukin-1*, (Alan R. Liss, Inc., New York, 1985; hereinafter cited as "Kluger Symposium") describe factors derived from human epidermal cells, designated epidermal cell thymocyte-activating factor (ETAF) and leukocytic pyrogen (LP), which appeared to be biochemically similar to IL-1. These factors were active as chemoattractants for polymorphonuclear (PMN) and mononuclear leukocytes (MNL). Since many inflammatory skin conditions are characterized by infiltration of PMN and MNL into the dermis, the authors suggested that ETAF, and possibly IL-1, played a role in the pathogenesis of inflammatory skin diseases. Gahring et al., in another paper published in the Kluger Symposium, supra, found measurable levels of ETAF in the strateum corneum, the outermost layer of the skin, and speculated that the presence of the factor in the strateum corneum provided a mechanism for immediate deposition of ETAF in a wound site and subsequent induction of inflammation.

Byars et al., *Fed. Proc.* 43: 426 (1984) found that supernatants of guinea pig macrophage cultures stimulated with muramyl dipeptide (MDP) were capable of inducing proliferation of capillary endothelial cells. However, the authors did not demonstrate that IL-1 in the culture supernatants was the mitogenic factor.

Bevilaqua et al., *J. Exp. Med.* 160: 618 (1984) described experiments in which partially purified IL-1 preparations were shown to induce procoagulant activity in cultures of human vascular endothelial cells.

Human IL-1 activity resides in two distantly related proteins, which are now known as IL-1α and IL-1β (March et al., *Nature* 315: 641 (1985)). Both molecules are normally synthesized as larger precursors having molecular weights of about 31,000 daltons, which are subsequently processed by proteolytic cleavage to yield mature forms having molecular weights of approximately 17,500 daltons. Although the proteins share only 26% homology, both molecules bind to the same cell surface receptor and in initial experiments appeared to possess coextensive biological activity. Recently, cDNA, coding for both human IL-1 species have been cloned and expressed in *E. coli*, which has enabled production of sufficient quantities of IL-1α and IL-1β for clinical evaluation.

However, the clinical utility of direct IL-1 application in aiding the process of wound healing has never been established. Due to the diversity of biological activities which have been attributed to IL-1, and the lack of understanding of the role of such activities in the healing process, the present state of the art does not allow one to predict whether IL-1 would retard or accelerate wound healing if applied topically to the site of injury.

It has now been found that IL-1 proteins are effective promoters of wound healing when applied to injuries in the form of a topical formulation comprising the protein.

SUMMARY OF THE INVENTION

The present invention provides topical compositions for the acceleration of wound healing in mammals, including humans, comprising a sufficient quantity of a mammalian interleukin-1 (IL-1) to promote wound healing, and a physiologically acceptable hydrophilic vehicle for application of the IL-1 to the site of injury. The present invention also includes the use of IL-1 for preparing a medicament for promoting wound healing in mammals, wherein the medicament is applied to a wound site.

BRIEF DESCRIPTION OF THE DRAWINGS

FIGS. 10-12 are graphs showing the extent (Gilman Index) of closure of decubitus ulcer wounds defore, during and after treated with 0.1 μg, 1.0 μg or 2.0 μg recombinant human IL-1β.

DETAILED DESCRIPTION OF THE INVENTION

Figure 1:
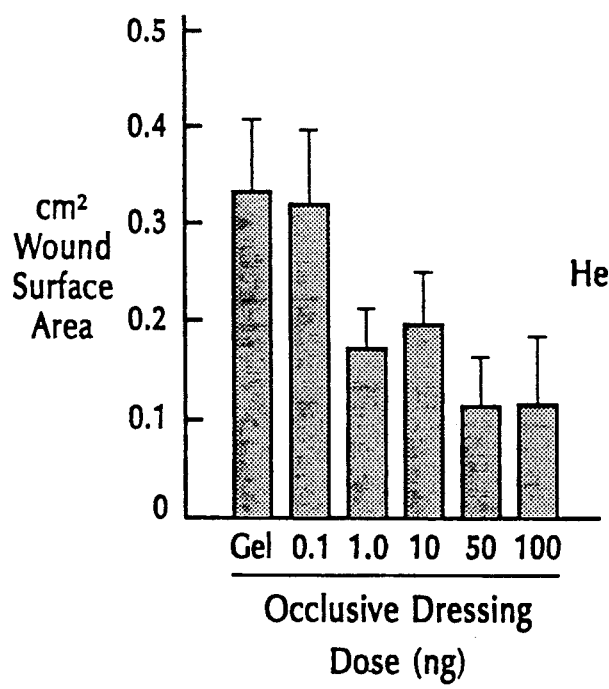
FIGS. 1 and 2 are graphs showing IL-1α dose responses over a 5 day period, as measured by wound surface area and percent healing, respectively.

The skin is the largest organ of warm-blooded organisms and provides a variety of critical homeostatic functions. When the structural integrity of the skin is compromised by a burn or laceration, a sequence of cellular events is initiated which generally results in closure of the wound and ultimately proliferation of new epidermal cells at the site of injury.

The first stage in wound healing involves closure of damaged blood vessels and platelet aggregation at the site of vascular damage. Coagulation of plasma fibrin, fibrinogen, fibronectin, other plasma and dermal proteins, proteoglycans and glycoproteins provides a solid substrate in the wound site. A second stage involves inflammation produced by the action of leukocytes and macrophages in the region of the wound, which remove bacteria and damaged cells, and which are also thought to secrete various soluble factors to aid in the regenerative process. The actual reconstruction of tissue at the wound site is initiated by fibroblasts, which adhere to the wound site, proliferate, and secrete collagen which is crosslinked to provide a structurally stable foundation for further healing. In mammals, the final stages of wound healing are accomplished by the mobilization of epidermal cells at the edges of the defect and their migration across the viable tissue in the site. Once the defect is covered, there is a process of differentiation, whereby the epithelial cells synthesize keratin and ultimately re-establish the structure of the epidermis.

There are a number of chronic or intractable wounding conditions which suggest a need for improving wound healing technologies. For example, methods of increasing the rate of healing of burns, chronic bedsores, ulcerative skin conditions, and other difficult-to-heal wounds would be of great interest to the practice of veterinary and human medicine. There are also disease states, for example, diabetes, which are marked by a retardation of natural wound-healing ability.

Current concepts in wound healing technology stress the use of moist, semiocclusive dressings during the initial stages of wound repair. Occlusion of a wound by applications of a polyethylene or polyurethane film keeps the wound moist while permitting gas exchange. Generally, the rate of epidermal healing is increased while pain is reduced.

With the advent of biotechnology and new methods for producing hormones and growth factors, a search has begun for growth factors which are useful in promoting wound healing. Among the factors which have been reported to be potentially beneficial wound healing promoters are transforming growth factor beta (TGF-$\beta$), epidermal growth factor (EGF), angiogenesis factor, and fibroblast growth factor (FGF). However, the actual effectiveness of such factors in clinical practice is only now being evaluated.

In accordance with the present invention, wound dressing compositions are formulated which comprise biologically effective quantities of interleukin-1 proteins in admixture with inert, hydrophilic vehicles, for example, aqueous gels. Such vehicles provide a means for applying the IL-1 to the wound site, provide a temporary reservoir of IL-1 at the wound site, and keep the wound site continually moist.

Either IL-1$\alpha$ or IL-1$\beta$ proteins may be used to prepare a medicament for providing wound healing in a mammal, including a human. IL-1 proteins are applied to the wound site in amounts effective in promoting wound healing. The wound healing compositions of this invention may comprise from 50 pg to 50 $\mu$g IL-1 ($\alpha$ or $\beta$) per gram of vehicle, preferably from 50 ng/g to 500 ng/g. A beneficial effect can be found at very low levels of IL-1, although greater quantities can be incorporated into particular formulations to account for protein degradation during formulation or storage.

Generally, IL-1 (IL-1$\alpha$, IL-1$\beta$ or both) may be effectively applied to a wound site to provide 5 day cumulative doses of IL-1 ranging from about 0.2 ng to about 1 $\mu$g/cm$^2$ wound surface area. Specifically, IL-1$\alpha$ or IL-1$\beta$ may be applied to the wound site to provide the following 5 day cumulative doses (listed in increasing order of preference): about 2 ng to about 500 ng, about 20 ng to about 400 ng, 50 ng to about 300 ng per cm$^2$ of wound surface area. Similarly, IL-1$\alpha$ and IL-1$\beta$ may be combined and applied to the wound site to provide the following 5 day cumulative doses (listed in increasing order of preference): 1 ng to about 250 ng IL-1$\alpha$ and 10 ng to about 200 ng IL-1$\beta$ per cm$^2$ wound surface area, 25 ng to about 150 ng IL-1$\alpha$ and 1 ng to about 250 ng IL-1$\beta$ per cm$^2$ wound surface area, 10 ng to about 200 ng IL-1$\alpha$ and 25 ng to about 150 ng IL-1$\beta$ per cm$^2$ wound surface area. Wound surface area is the area defined by the perimeter of the wound, and can be estimated by multiplying the length and width of the wound. More accurate measurement of wound surface area can be obtained by use of a planimeter (Houston Instruments).

Doses will vary depending on the depth or type of wound. Although deeper and more severe wounds would normally be expected to require higher doses of IL-1, lower doses may be used on wounds characterized by damaged vasculature. Doses will also vary depending on whether the health of the individual being treated is normal or impaired. Impaired individuals, for example, include those with chronic bedsores, ulcerative skin conditions, diabetes or other metabolic diseases, and those who are aged, malnourished, immunodeficient, are undergoing corticosteroid or chemotherapy treatment, or who abuse chemical substances. It is anticipated that such individuals with impaired health will require higher doses of IL-1 to treat wounds and that the individual will be treated for relatively longer periods of time.

Examples of suitable aqueous inert vehicles for use in formulating the compositions of the invention include collagen, carboxymethyl cellulose, hydroxyethyl cellulose, or other cellulosic compounds, or gels prepared from a mixture of polyethylene glycols. Due to the requirement for biocompatibility and absorption of the gel by intact or damaged skin, suitable compounds for vehicle formulation will generally be cellulosic derivatives. A variety of long chain compounds are commercially available in a range of viscosities for this application. Vehicle components can be sterilized by autoclaving prior to formulation. IL-1 solutions are preferably sterilized by gamma irradiation (1.5 mrads).

A variety of additives may be incorporated into the compositions of the present invention, provided that they do not deleteriously affect IL-1 biological activity. Stabilizers or preservatives, such as mixtures of metyl and propyl parabens, are useful in preventing adventitious microbial contamination during formulation and storage. Antioxidants such as BHT, BHA, or others may be useful in precluding degeneration of IL-1 proteins in the final formulation. Protease inhibitors such as $\alpha$-antitrypsin inhibitor, $\alpha_2$-macroglobulin, soybean trypsin inhibitor, phenylmethylsulfonyl fluoride, various halomethyl ketone peptidyl compounds, or mixtures thereof, may be useful in preventing degradation by proteolytic agents. Chelating agents such as EDTA may be employed if the final product is stored in metal tubes, in order to reduce the possibility of reaction of the active interleukin-1 ingredients with metal ions.

Dyes also may be added to IL-1 protein mixtures before they are mixed with the gel. To assure product homogeneity, the gel is mixed until a uniform absorbance at the dye's absorbance peak is achieved. This avoids the need to conduct relatively cumbersome biological assays for the small quantities of IL-1 proteins present in the final product.

Sources of Recombinant Interleukin-1 Proteins

As used herein, "interleukin-1", "recombinant interleukin-1", "IL-1" and "rIL-1" refer collectively to mammalian IL-1 proteins having amino acid sequences substantially identical to those of native mammalian forms of IL-1α and IL-1β, and which possess biological activity in common with the native forms. Substantial identity of amino acid sequences means that the sequences are identical or differ by one or more amino acid alterations (deletions, additions, or substitutions) that do not cause an adverse functional dissimilarity between the synthetic protein and the native form. Preferably, recombinant forms of mammalian IL-1α and IL-1β proteins are employed in formulating the compositions of the invention. Such recombinant proteins can be conveniently produced by microbial fermentation processes, for example, in Saccharomyces or preferably in E. coli, as described below.

Mature human IL-1α and IL-1β can be expressed in E. coli under the control of the phage λPL promoter and cI857ts thermolabile repressor. Expression plasmids for rIL-1α and rIL-1β production can be constructed from plasmid pPLc28 (ATCC 53082), plasmid pKK2233 (available commercially from Pharmacia Fine Chemicals, Uppsala, Sweden) and plasmids containing IL-1α clone 10A (March et al., supra; ATCC 39997) and IL-1β clone IL-1-14 (ATCC 39925) as follows.

To create an expression vector for IL-1α, a 3' portion of the IL-1α gene, extending from $Ser^{113}$ (nucleotides 337-339) to $Ala^{271}$ (nucleotides 811-813), is inserted into expression vector pPLc28. This is achieved by excising a 499 base pair AluI-NdeI fragment from the 10A clone, to which the following synthetic oligonucleotide linker is joined:

```
AATTCTAGGATAATTA ATG TCA GCA CCT TTT AG
    GATCCTATTAAT TAC AGT CGT GGA AAA TC
```

This linker includes AluI and EcoRI termini, a ribosome binding site, and an ATG initiation codon in addition to the IL-1α $Ser^{113}$-$Ser^{117}$ sequence. pPLc28 is then digested to completion with EcoRI and NdeI, and the resulting larger fragment isolated by agarose gel electrophoresis. The linker, 10A clone, and plasmid fragments are then fused using T4 ligase to provide an expression plasmid denoted pILα. Additional details of the construction of pILPα can be found in the disclosure of published European Patent Application 188,864, the relevant disclosure of which is incorporated by reference herein.

The resulting construct is then employed to transform E. coli strain ΔH1 (ATCC 33767; Castellazi et al., Molec. Gen. Genet. 117: 211) to ampicillin resistance, using standard techniques. To express the plasmid-borne IL-1α gene, cultures of transformed ΔH1 are grown in L-broth without ampicillin. When the cultures reach an $A_{720}$ of about 0.5, the culture temperature is raised to about 42° C. to promote derepression of the thermolabile PL promoter. After one hour at elevated temperature, cells are harvested by centrifugation and flash-frozen in a dry-ice/methanol mixture.

Recombinant human IL-1β can be produced using another plasmid, herein designated pILPβ. This vector is assembled from pILPc (March et al., supra), which is constructed by replacing the BamHI/EcoRI fragment of pKK223-3 with a Sau3A/EcoRI fragment from pPLc28 containing the λPL promoter. This plasmid is digested to completion with EcoRI and PstI, and the largest fragment then ligated to (1) a 669 base pair HpaII/PstI fragment from pIL-1-14 (ATCC 39925) containing the human IL-1β gene ($Ala^{117}$ to COOH terminus encodes active protein) and (2) the following EcoRI/HpaI synthesis oligonucleotide:

```
AATTCTAGGATAATTA ATG GCA CCT GTA CGA TCA CTG AAC TGC ACG CTC
    GATCCTATTAAT TAC CGT GGA CAT GCT AGT GAC TTG ACG TGC GAG GC
```

Plasmid pILPβ is then used to transform E. coli H1 or other cells containing a thermolabile repressor of $P_L$ transcription. Following growth to $A_{720}$ of about 0.5, expression of the rIL-1β gene is obtained by heat induction as previously described. rIL-1β activity, as in the case of rIL-1α, can be identified using the thymocyte mitogenesis or IL-1 conversion assays cited above.

Recombinant human IL-1 proteins can be isolated from crude bacterial extracts by acid extraction in appropriate buffers. Cells can be disrupted by any convenient method, including freeze-thaw cycling, sonication, mechanical disruption, or use of cell lysing agents. Preferably, the acid-mediated extraction step for rIL-1α is conducted in an aqueous buffered medium having a pH from about 2.0 to about 3.5, and most preferably, at a pH from about 2.6 to about 3.0. In the case of rIL-1β, the acid extraction step is preferably conducted at a pH from about 3.5 to about 4.5, and most preferably, at a pH from about 3.7 to about 4.1.

To complete purification, the initial acid extraction step is followed by chromatography in aqueous media. This part of the purification process may include an initial ion exchange chromatography stage followed by affinity chromatography. The ion exchange stage comprises, in a preferred aspect, cation exchange chromatography followed by anion exchange chromatography.

Suitable cation exchange chromatography media include various insoluble matrices comprising sulfopropyl or carboxymethyl groups. Sulfopropyl groups are preferred. The matrices can be acrylamide, agarose, dextran, cellulose or other ion exchange resins or substrates commonly employed in protein purification. A particularly useful material for cation exchange chromatography of rIL-1α and rIL-1β is Sulphopropyl Sephadex C-25 (Pharmacia Fine Chemicals, Uppsala, Sweden). When media containing sulfopropyl groups are employed, extracts containing rIL-1 species are applied at a pH of about 4.0, in a suitable buffer such as sodium citrate. rIL-1 species are bound by the ion exchanger, and can be eluted in more highly purified form by application of a weakly basic eluant, for example, 10 mM Tris-HCl, pH 8.1.

Suitable anion exchange chromatography media include various insoluble matrices comprising diethylaminoethyl (DEAE) or diethyl-(2-hydroxypropyl)aminoethyl (QAE) groups. DEAE groups are preferred. The matrices can be acrylamide, agarose, dextran, cellulose or other types commonly employed in protein purification. A particularly useful material for cation exchange chromatography of rIL-1α and rIL-1β is DEAE-Sephacel (Pharmacia). When media containing DEAE groups are employed, extracts containing rIL-1 species are applied at a weakly basic pH. For example, the pooled rIL-1-containing fractions resulting from the previous cation exchange chromatography step (at a pH of about 8.1) can be applied directly in a suitable buffer such as Tris-HCl. rIL-1 species are bound by the anion exchange media, and can be eluted in more highly purified form by application of a salt gradient in the same buffer. It has been determined that rIL-1α elutes from DEAE-Sephacel at 0.17–0.22M NaCl, and rIL-1β at 0.075–0.155M NaCl. Thus, gradients ranging from 0 to 600 mM NaCl and 0 to 400 mM NaCl are useful in purifying rIL-1α and rIL-1β, respectively.

The foregoing extraction and ion-exchange chromatography procedures are followed by affinity chromatography. For IL-1α, affinity media comprising pendant phenyl glycidyl ether groups such as Phenyl Sepharose CL-4B (Pharmacia) can be employed. rhIL-1α is applied to such media in a solution containing about 0.5 to 0.7M (preferably about 0.6M) ammonium sulfate, in a suitable buffer at a pH of about 8.1, and then eluted with a decreasing linear gradient of ammonium sulfate followed by buffer containing no salt. rhIL-1α elutes from Phenyl Sepharose CL-4B at about 0.25–0.10M ammonium sulfate.

For the final affinity step for purifying IL-1β, affinity media comprising pendant triazinyl red dye ligand groups such as Procion Red agarose (Bethesda Research Laboratories, Gaithersburg, Md. U.S.A.) can be employed. Pooled fractions containing rIL-1β are applied to the dye-ligand media at a low ionic strength, e.g., less than 40 mM, in a suitable buffer such as 10 mM Tris-HCl. The media comprising bound rIL-1β is then washed with additional application buffer, and the desired protein eluted in a linear gradient of increasing salt concentration, e.g., 0 to 1M NaCl. rIL-1β elutes from Procion Red at about 0.36–0.46M NaCl. The resulting fractions can be concentrated by a final chromatography step on media containing pendant sulfopropyl groups.

IL-1 activity in cell extracts and during purification can be assayed by either a thymocyte mitogenesis assay or an assay of IL-1 induced IL-2 production, as described by Conlon, *J. Immunol.* 131:1280 (1983) and Kronheim et al., *J. Exp. Med.* 161:490 (1985). SDS-PAGE can also be employed to monitor purification progress, substantially as described by Kronheim et al., supra.

EXAMPLE 1

Effect of Topical Application of Human Interleukin-1 on Wound Healing in Mice The following experiment was designed to evaluate the effect of IL-1 on granulation tissue production and wound closure and to investigate potential modes of application.

Forty female Swiss CB mice (Charles River Breeding Labs, Boston, Mass.) were used in this study. Mice were caged individually for a period of one (1) week prior to initiating the experiment and throughout the experimental period (4 weeks). These animals were fed a basal diet ad libitum and kept in a controlled (temperature 19°–21° C., 12 h light, 12 h dark cycle and 50% relative humidity) environment.

Twenty mice were used to determine the effect of IL-1α on granulation tissue production. In this approach, porous wound chambers were implanted in a wound site and examined later for cellular ingrowth. Wound chambers were made from Ivalon ® sponges made of polyvinyl alcohol and formaldehyde. To implant the chambers, each mouse was anesthetized under light ether and a 3×3 cm square of dorsal skin swabbed with an antiseptic. A 1 cm incision was made in the dorsal neck skin. The sterile wound chamber was inserted subcutaneously, aligned paravertebrally, and the incision closed with two interrupted sutures.

Twenty-four hours after subcutaneous implantation of the wound chambers, the 20 mice were divided into three (3) treatment groups. Group A received a 1 ml subcutaneous injection of the IL-1α 15 ng/ml in PBS buffer containing 1% bovine serum albumin (BSA). The agent was injected directly into the wound chamber. Group B wound chambers were injected with 1 ml of 60 ng/ml IL-1α-PBS-BSA solution. Group C chambers were injected with control solution in PBS-BSA buffer. The wound chambers were treated once only.

Ten days after treatment, the mice were sacrificed and the wound chambers harvested and assayed histologically as follows. A four millimeter (4 mm) cylindrical portion of the wound chamber including its capsule were fixed in formalin and embedded in paraffin. Four micron sections were then stained and examined qualitatively for the ingrowth of cells and connective tissue.

Upon examination of sections from the 10 day-old wound chambers a clear difference could be seen between chambers treated with IL-1α and control solutions. Chambers treated with the active agent had significantly more cellular infiltration than did control chambers. Only slight differences were seen between chambers treated with 15 ng and those treated with 60 ng of IL-1α. The IL-1α treated chambers had a much thicker capsule around the implant when compared with controls. There was also a significant difference in the amount of new connective tissue deposited within and throughout the chamber. Chambers treated with IL-1α (at either concentration) displayed significantly more connective tissue accumulation than did control specimens.

In a second experiment, mice were anesthetized and prepared for surgery as described previously. Two full thickness skin wounds were made with a 6 mm biopsy punch on each experimental animal. The animals were divided into four 4 groups and treated as follows: Group A had one wound treated with 15 ng of the active agent in a PBS-BSA buffer solution and the other wound treated with a control solution consisting of buffer only. Group B had one wound treated with 60 ng of IL-1α in a PBS-BSA solution and the other treated with control solution only. Group C had one wound treated with 60 ng of the active agent blended in a hydrophilic vehicle (Aquaphor ®, Biersdorf Inc.), and the other wound was treated with the vehicle and the control solution. Group D mice had one wound treated with the hydrophilic vehicle alone (Aquaphor ®) while the other wound remained untreated.

All wounds were dressed after treatment with copolyester film backed with a pressure sensitive adhesive (Co-Film ®) dressing (Chesebrough-Ponds Inc.). Wounds were only treated once. All wounds were evaluated every other day by serial photography and wound closure measured by planimetry. All data was evaluated using the Student's t-test for paired comparisons.

The effect of IL-1α on the rate of wound closure varied with respect to whether the protein was presented in the hydrophilic vehicle or not. Wounds treated with IL-1α (60 ng) in the hydrophilic vehicle (Group C) closed more rapidly than did wounds treated with a vehicle-only control. Statistical significance ($p<0.05$) between healing rates of wounds treated with IL-1α in the hydrophilic vehicle (Group C) and those treated with the hydrophilic vehicle only was achieved on day 12 and day 15 after wounding. Wounds treated with IL-1α at either 15 ng or 60 ng (A or B) in a PBS-BSA vehicle healed somewhat more slowly than wounds treated with the hydrophilic vehicle only during the entire course of the experiments although the difference was not statistically significant. No significant differences were seen between the healing rates of wounds treated with IL-1α in a PBS-BSA buffer alone and untreated controls (Group D).

The wounds treated with the active agent or the control solution in a PBS-BSA buffer healed more slowly than did wounds that were kept moist by treatment with the hydrophilic ointment base. The wounds treated with the aqueous base vehicle (PBS-BSA) with or without IL-1α were dry 24 hours after the film dressings were removed. In contrast, the wounds treated with the ointment base remained moist for a longer period of time. A dry crust developed on the wounds treated with the aqueous vehicle. This thick eschar remained on the wound throughout most of the healing period. The ointment treated wounds (with or without IL-1α) had a thinner, softer eschar which was sloughed between day 9 and day 12 after wounding.

Overall, wounds treated with IL-1α in the hydrophilic ointment base were re-epithelialized approximately 6 days before the other treatment groups.

EXAMPLE 2

Effect of Topically Applied Human Interleukin-1 on Healing of Partial Thickness Wounds in Pigs This single blind in vivo study was designed to evaluate the effect of topically applied hydrophilic gels containing IL-1α and IL-1β on the healing of partial thickness wounds.

Bulk concentrations of rhIL-1α and rhIL-1β were formulated in a topical gel containing carboxymethyl cellulose and propylene glycol. The IL-1/buffer solution was aseptically added to the gel using an Eppendorf pipetter under a laminar flow hood. The gel was then stirred with a Teflon spatula for approximately 3 seconds. Plungers were removed from sterile 5 ml plastic syringes, and the gel was dispensed into these syringes from the top. The plungers were then replaced. All processing was done aseptically and in a laminar flow hood. Appropriate dilutions of the IL-1α and IL-1β were made and aliquots were added to the gel to make the following concentrations (weight protein/weight gel):

| | | |
|---|---|---|
| IL-1α | 40 ng/g | (1) |
| | 200 ng/g | (2) |
| | 2 μg/g | (3) |
| IL-1β | 40 ng/g | (4) |
| | 200 ng/g | (5) |
| | 2 μg/g | (6) |

Six young Yorkshire pigs weighing approximately 10 kg each were fed a basal diet ad libitum and housed individually in a facility under controlled conditions (19°–20° C., 12 hr light, 12 hr dark cycle, 65% relative humidity). Each animal was clipped with standard animal clippers. The skin on both sides of the animal was prepared for wounding by washing with sterile saline. The animals were anesthetized using pentobarbital sodium (Nembutal ® sodium 12/mg/kg i.p.) and approximately 120 wounds measuring 7×10 mm and 0.3 mm deep were made in the paravertebral and thoracic area with an electrokeratome as described in Alvarez et al., *J. Plast. & Reconstr. Surg.* 69:284 (1982). The wounds were separated from one another by at least 15 mm of normal skin.

The wounds on each animal were divided into 8 groups and treated as follows: control (no treatment), vehicle gel (placebo) and six treatment groups including 40 ng/g, 200 ng/g and 2 μg/g recombinant human IL-1α and 40 ng/g, 200 ng/g and 2 μg/g recombinant human IL-1β. At least 2 cm of normal skin separated each of the treatment groups. Immediately after wounding, the wounds were treated with 0.2 ml of the appropriate agent, assuring that the agent covered the entire wound. In order to rule out the possibility that wounds made in different anatomical regions might heal differently, the regions selected for each treatment were varied among animals.

Each day after wounding (day 0) for a period of 6 days, several wounds and surrounding normal skin from each treatment group were excised at 0.5 mm using an electrokeratome equipped with a 2 mm blade as described by Alvarez et al., *Arch. Dermatol.* 119:222 (1983). The excised skin containing the wound site was incubated in 0.25% trypsin for 12–24 hours at 4° C. to separate the dermis from the epidermis. The epidermal migration was assessed as described by Alvarez et al., *J. Invest. Dermatol.* 81:144 (1983). Briefly, this method is a macroscopic examination of the separated epidermis for defects. Defects are visualized as holes in the separated epidermal sheet or as a lack of epidermal continuum in the area that contained the wound. The wound is considered re-epithelialized if there are no defects in the epidermis and not re-epithelialized if there are one or more defects.

All of the data were statistically analyzed using Student's t-test as described in Alvarez et al., *Arch. Dermatol.* 119:222 (1983). Probit analysis was performed according to the method of Zar as described in Alvarez et al., *J. Invest. Dermatol.* 81:144 (1983).

The data obtained is indicated in Table 1, below, and all values are expressed as the number of specimens healed per total number of specimens examined at each point in time. The numbers in parentheses represent the percent healed.

TABLE 1

Effect of Hydrophilic Gels Containing rhIL-1α and rhIL-1β on the Healing of Partial Thickness Wounds

| Treatment | Number (and Percent) of Specimens Healed Days After Wounding | | | | |
|---|---|---|---|---|---|
| | 2 | 3 | 4 | 5 | 6 |
| IL-1α | | | | | |
| 40 ng/g | 0/10 | 12/31 | 16/26 | 19/21 | 9/9 |

TABLE 1-continued

Effect of Hydrophilic Gels Containing
rhIL-1α and rhIL-1β on the Healing of Partial Thickness Wounds

| Treatment | Number (and Percent) of Specimens Healed Days After Wounding | | | | |
|---|---|---|---|---|---|
| | 2 | 3 | 4 | 5 | 6 |
| 200 ng/g | 0/6 (0%) | 0/26 (29%) | 11/23 (81%) | 20/24 (90%) | 11/11 (100%) |
| 2 μg/g | 0/7 (0%) | 0/32 (0%) | 12/28 (43%) | 15/18 (83%) | 19/19 (100%) |
| IL-1β | | | | | |
| 40 ng/g | 0/4 (0%) | 12/25 (48%) | 19/25 (76%) | 17/19 (89%) | 13/13 (100%) |
| 200 ng/g | 0/7 (0%) | 8/20 (30%) | 19/30 (63%) | 20/20 (100%) | 8/6 (100%) |
| 2 μg/g | 0/8 (0%) | 18/26 (88%) | 25/29 (86%) | 16/18 (100%) | 8/8 (100%) |
| Vehicle Only | 0/6 (0%) | 0/22 (0%) | 10/27 (49%) | 17/22 (77%) | 9/9 (100%) |
| Untreated | 0/3 (0%) | 0/15 (0%) | 3/30 (10%) | 7/15 (47%) | 14/19 (74%) |

A comparison of the relative rates of healing between the treatment groups and the control groups is provided in Table 2, below. In Table 2, "HT50" represents the number of days required for 50% of the wounds to heal.

TABLE 2

Healing Rates of Untreated Wounds and
Wounds Treated with Recombinant Human IL-1α and IL-1β

| Treatment | HT50 (Days) | Relative Rate of Healing Compared to: | |
|---|---|---|---|
| | | Untreated (%) | Vehicle Only (%) |
| IL-1α | | | |
| 40 ng/g | 3.5 | +30 | +13 |
| 200 ng/g | 4.1 | +18 | −3 |
| 2 μg/g | 4.2 | +16 | −5 |
| IL-1β | | | |
| 40 ng/g | 3.1 | +38 | +23 |
| 200 ng/g | 3.5 | +30 | +13 |
| 2 μg/g | 2.8 | +44 | +30 |
| Vehicle Only | 4.0 | +20 | — |
| Untreated | 5.0 | — | −25 |

This data indicates that IL-1β at 2 μg/g of gel increased the healing of partial thickness wounds by 44% over untreated and 30% over vehicle treated wounds. In addition, IL-1β at both 40 ng/g of gel and 200 ng/g gel also significantly accelerated the healing rate of the wounds (for example, 33% over untreated, 23% over vehicle treated at 40 ng/g). IL-1α provided similar, but quantitatively less, promotion of wound healing under the conditions tested. Finally, all wounds treated with a topical agent healed more rapidly than untreated controls which were left open to the air.

EXAMPLE 3

Effect of Topical Application of Human IL-1 on Wound Healing in Rats at Low Dosages The following experiment was a single blind study designed to evaluate the effect of IL-1 on wound closure and, more particularly, to investigate healing response at various dosages of IL-1.

Thirty-five (35) specific pathogen-free, normal female Lewis rats (Charles River Raleigh, Raleigh, N.C.) were used in this study. Rats were caged individually for a period of one week prior to initiating the experiment and throughout the experimental period (one week). These animals were fed a basal diet ad libitum and kept in a controlled environment (temperature 19°–21° C., 12 h light, 12 h dark cycle and 50% relative humidity).

All rats were prepared for surgery by anesthetizing with an intraperitoneal injection of ketamine/rompun. The surgical area was shaved, washed with iodine soap, and rinsed thoroughly with a sterile saline solution. Sterile drapes, gloves and instruments were used to achieve a sterile field.

Four full thickness incisional wounds (1.5 cm in length, 0.3 cm wide and about 0.2 cm deep to the muscle fascia) were made with a #15 surgical blade on the dorsal skin of each experimental animal to create an elliptically shaped wound having a surface area of approximately 0.5 cm$^2$. Wounds remained unsutured throughout the experiment. For purposes of quantifying IL-1 dose response by wound surface area, the surface area of each wound was estimated by multiplying maximum length and maximum width of the elliptically shaped wound. The wounds were separated from one another by at least 2 cm of normal skin.

For topical application of IL-1, a carboxymethylcellulose (CMC) gel was formulated as follows. 25 g of glycerol and 25 g of propylene glycal were mixed with 0.1 g of propyl-p-hydroxybenzoate and 1 g methyl-p-hydroxybenzoate. 950 ml of sodium phosphate buffer (0.1M, pH 6.0) was then added to the mixture. The resulting solution was stirred until smooth and filtered through a 0.22 micron filter. 30 g of autoclaved CMC was then added to the filtered buffer. The final yield of the CMC vehicle gel was about 1000 g. Purified sterile recombinant human IL-1α or IL-1β was added to aliquots of the CMC vehicle gel to a final concentration of 0.1 ng, 1.0 ng, 10 ng, 50 ng or 100 ng IL-1α or IL-1β per 50 μl of gel.

Immediately after wounding, wounds were treated as follows. Control wounds were not treated. Placebo control wounds were directly treated with 50 μl of CMC vehicle gel alone. Test wounds were directly treated with 0.1 ng, 1.0 ng, 10 ng, 50 ng or 100 ng of either IL-1α or IL-1β in 50 μl CMC vehicle gel at each wound site. Each wound was treated only once.

The animals were divided into 7 groups of 5 animals each and treated as follows: Group A had two wounds treated with vehicle only and two wounds treated with 0.1 ng IL-1α in vehicle. Group B had two wounds treated with 1.0 ng IL-1α in vehicle and two wounds treated with 10 ng IL-1α in vehicle. Group C had two wounds treated with 50 ng IL-1α in vehicle and two wounds treated with 100 ng IL-1α in vehicle. Group D had two wounds which were untreated and two wounds treated with vehicle only. Groups E, F and G had wounds treated with IL-1β in the same concentrations as IL-1α used to treat Groups A, B and C, respectively. In order to maintain a sterile field, wounds were covered with occlusive dressings comprising Telpha ® compacted gauze pads and an Op Site ® polyurethene adhesive covering. All wounds treated with IL-1α or IL-1β had occlusive dressings. Only rats in group D, which had untreated and placebo treated wounds, were not covered with occlusive dressings in order to observe whether the absence of occlusive dressing had an effect on wound healing.

Five days after treatment, the animals were sacrificed. The dressings were then removed from the wounds and the wounds were visually examined to qualitatively determine the effects of treatment upon wound healing as measured by percent healing compared to the original wound. Percent healing was measured by visually inspecting and rating each wound as 0%, 25%, 50%, 75% or 100% healed, with 0% healing showing an open wound with no signs of healing and 100% healing showing a completely healed wound with reepithelialization observed without scab formation. Other criteria used to determine percent wound healing included wound color, wound surface area, indications of swelling or infection, and presence of granulation tissue as observed from the exterior of the animal. Wound surface area was measured in the same manner as the original wounds were measured (described above) and the data was used to calculate the unhealed wound surface area. Thus, each wound was rated according to a visual estimate of percent healing and unhealed wound surface area.

The resulting data were statistically analyzed using the Students' t-test as described in Alvarez et al., Arch. Dermatol., 119:222 (1983). Each treatment or control group consisted of 10 wounds. The data is accordingly represented as the mean ±SEM for n=10.

Figure 3:
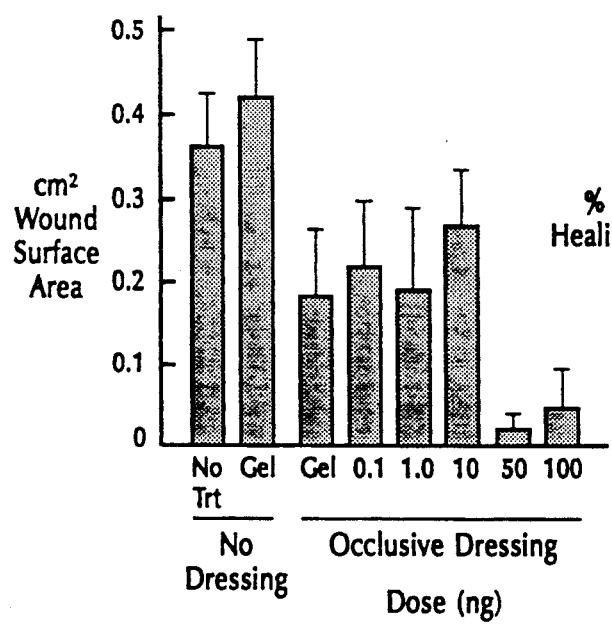
FIGS. 3 and 4 are graphs showing IL-1β does responses over a 5 day period, as measured by wound surface area and percent healing, respectively.

The data obtained by measuring wound surface area after five days are represented graphically in FIGS. 1 and 3. FIG. 1 indicates that application of IL-1α resulted in significant wound healing (compared with placebo treated wounds) at the 10 ng dose, as measured by reduction in wound surface area. FIG. 3 indicates that application of IL-1β resulted in significant wound healing (compared with the untreated wounds and placebo treated wounds) at the 50 ng dose of IL-1β, as measured by reduction in wound surface area. The data shows that dosages of IL-1α as low as about 1.0 ng and dosages as low as about 50 ng of IL-1β are effective in promoting wound healing.

Figure 2:
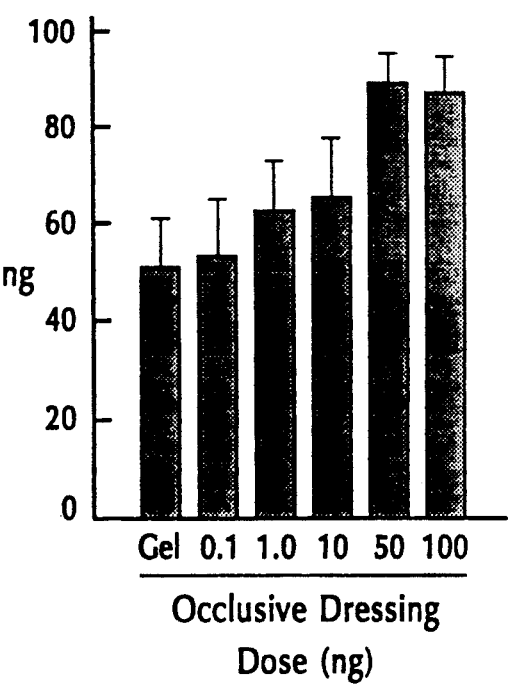
Figure 4:
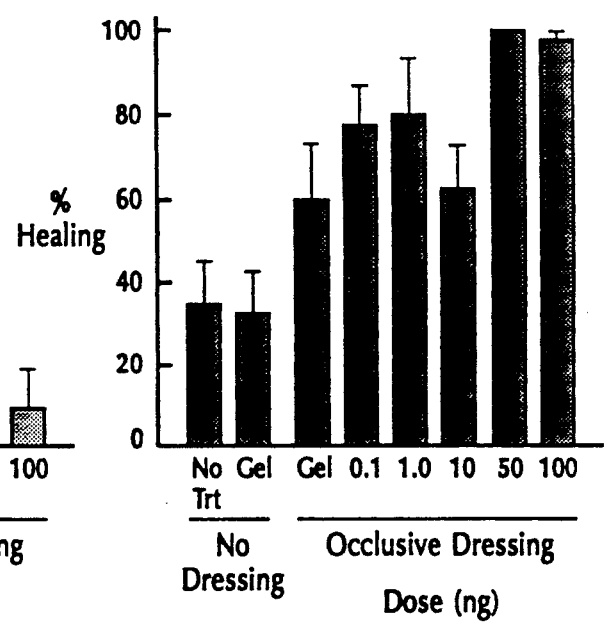

The data obtained by observing percent healing after five days are represented graphically in FIGS. 2 and 4. FIGS. 2 and 4 indicate that wounds treated with either 50 ng or 100 ng of IL-1α or IL-1β healed significantly faster than placebo treated wounds.

EXAMPLE 4

Effect of Topical Application of Human IL-1 on Burn Wounds in Pigs

A study was conducted to determine the effect of topically applied recombinant human IL-1β gel with reconstituted, lyophilized IL-1 on second degree burn healing in pigs. Twelve young specific pathogen free (SPF) pigs weighing 20-25 kg were used in the study. Each pig was housed individually in facilities meeting American Association for Accreditation of Laboratory Animal Care (AAALAC) compliance standards with controlled temperature (19°-20° C.) and light and dark (12 h/12 h LD) and received water and a basal diet without antibiotics (Purina Control Factor) ad libitum for a period of two weeks prior to experimentation.

Prior to wounding, each pig was clipped with standard animal clippers and the skin on the back and both sides was prepared for wounding by washing with a non-antibiotic soap (Neutrogena ®).

On the day of wounding (day 0), the pigs were anesthetized with ketamin (I.M.) and inhalation of a halothane, oxygen and nitrous oxide combination. A specially designed cylindrical brass rod weighing 358 g was heated in a boiling water bath to 100° C., wiped dry to prevent water droplets from creating a steam burn on the skin, and applied to the skin surface in a vertical position, with all pressure supplied by gravity, for a period of six seconds, to make a burn wound 8.5 mm diameter ×0.6 mm deep. Immediately after burning, the roof of the burn blister was removed with a sterile spatula. Approximately 110-120 burn wounds were made approximately 2 cm from each other on the anterior two-thirds of the pig.

The pigs were divided into the following treatment groups:

| Number of Animals | Treatment Groups |
| --- | --- |
| 2 | 1) air exposed control<br>2) IL-1 (2 μg/ml) in gel with occlusion, or<br>3) gel with occlusion |
| 2 | 1) air exposed control<br>2) gel with occlusion, or<br>3) occlusion only |
| 2 | 1) air exposed control<br>2) IL-1 (2 μg/ml) in gel with occlusion, or<br>3) occlusion only |
| 2 | 1) air exposed control<br>2) lyophilized IL-1 (2 μg/ml) in vehicle with occlusion, or<br>3) vehicle with occlusion |
| 2 | 1) air exposed control<br>2) vehicle with occlusion, or<br>3) occlusion only |
| 2 | 1) air exposed control<br>2) lyophilized IL-1 (2 μg/ml) in vehicle with occlusion, or<br>3) occlusion only |

Approximately 50 μl of test agent was applied topically to each wound site. All treatment groups except for air exposure was occluded with a polyurethane dressing (Op Site ®). The dressings were secured on the animals with an ace bandage wrap. On days 1 and 2 post wounding each group was treated with an additional 50 μl of test agent by injection through the polyurethane dressing. A small patch of dressing was placed over the injected area.

On days 7-14, five burn wounds from each treatment group were surgically excised using an electrokeratome (0.6 mm deep). The excised burn wounds and the surrounding normal skin was incubated in 0.5M NaBr for 24 hours at 37° C. After incubation, the specimens were separated into epidermal and dermal sheets. The epidermis was then examined macroscopically for defects in the area of the burn wounds. Epithelialization was considered complete if no defect was present (healed); any defect in the burn area indicated that healing was incomplete.

Tables 3-4 show the results of this study. Table 3 shows that 50 μl of IL-1 gel on each wound (2 μg of IL-1 per ml of gel or water, for a total dose of 0.14 μg IL-1 per $cm^2$ of wound area) accelerated wound healing relating to gel placebo. Table 4 also shows that IL-1 gel accelerated wound healing.

TABLE 3

The Effect of Different Concentrations of IL-1 on Epidermal Wound Healing Days After Wounding

| Treatment | 6 | 7 | 8 | 9 | 10 | 11 | 12 | 13 |
| --- | --- | --- | --- | --- | --- | --- | --- | --- |
| Air Exposed | 1/40 (2%) | 3/60 (5%) | 3/59 (5%) | 25/59 (42%) | 40/57 (70%) | 51/56 (91%) | 47/51 (92%) | 47/47 (100%) |
| IL-1 gel | 1/19 | 1/19 | 7/19∞ | 16/18∞ | 15/15#* | | | |

TABLE 3-continued

The Effect of Different Concentrations of IL-1 on Epidermal Wound Healing Days After Wounding

| Treatment | 6 | 7 | 8 | 9 | 10 | 11 | 12 | 13 |
|---|---|---|---|---|---|---|---|---|
| Gel | (5%)<br>2/20 | (5%)<br>1/20 | (37%)<br>7/20∞ | (89%)<br>13/20 | (100%)<br>14/20 | 15/15 | | |
| placebo | (10%)<br>0/9 | (5%)<br>1/20 | (35%)<br>0/18 | (65%)<br>6/17 | (70%)<br>16/18 | (100%)<br>18/18 | | |
| IL-1 aq. | (0%) | (5%) | (0%) | (35%) | (89%) | (100%) | | |
| Aq. | 0/9 | 0/20 | 1/17 | 17/17~ | 17/17#* | | | |
| placebo | (0%) | (0%) | (6%) | (100%) | (100%) | | | |
| Opsite | 0/19 | 0/39 | 8/38* | 19/38 | 27/38 | 32/32 | | |
| | (0%) | (0%) | (21%) | (50%) | (71%) | (100%) | | |

∞P < 0.005 significance compared to air
~P < 0.001 significance compared to air
*P < 0.05 significance compared to air
P < 0.05 significance compared to Opsite

TABLE 4

The $HT_{50}S$ and Relative Rates of Healing Using IL-1

| Treatment | $HT_{50}$# | Relative Rate of Healing Compared to Air Exposed* |
|---|---|---|
| Air Exposed | 9.1 | |
| IL-1 gel | 7.8 | +14% |
| Gel placebo | 8.2 | +10% |
| IL-1 aq. | 8.8 | 3% |
| Aq. placebo | 8.1 | +11% |
| Opsite | 8.8 | 3% |

The times it takes for 50% of the wounds to epithelialize
*($HT_{50}$ Control - $HT_{50}$ Treatment) × 100 ($HT_{50}$ Control)

EXAMPLE 5

Effect of Topical Application of Human IL-1 on Pressure Sores in Humans Aged 18–50

A study was conducted to determine the effect of topically applied recombinant human IL-1β gel in adults aged 18–50 with stage II (skin broken through to dermis) or stage III (skin broken, invading subcutaneous tissues) decubitus ulcerations (pressure sores). The IL-1β used in this study was formulated in a recombinant human IL-1β gel, produced as described above in Example 3. A total of fifteen patients (divided into five groups of three patients) participated in the study. Each group received one of five dosages of recombinant human IL-1β gel (0.2, 1.0, 2.0, 4.0 and 6.0 μg/wound/day) applied daily in a 2 cc volume of gel to a single decubitus ulceration for a period of 14 consecutive days.

The effect of the IL-1β gel on wound healing was measured by the method of Gilman, Wounds 2:95, 1990, which utilizes the parameter $\bar{d}=\Delta A/\bar{p}$(the "Gilman index") as the measure of wound healing progress over given period of time. The parameter $\bar{d}=\Delta A/\bar{p}$, where ΔA is the change in wound area and p is the average of the wound perimeters before and after the study time period, represents the linear advance of the wound margin toward the wound center, and gives a valid comparison of healing progress for wounds of all shapes and sizes. The Gilman indices for wounds treated with IL-1β gel as described above, are shown below in Table 5.

TABLE 5

Healing Rates of Decubitus Ulcer Wounds Treated with Recombinant Human IL-1β

| Dose | Patient | Gilman Index (cm) | | |
|---|---|---|---|---|
| | | Pre-treatment | Treatment | Post-Treatment |
| 0.1 μg | 1 | −0.22 | +0.23 | −0.33 |
| | 2 | +0.09 | +0.40 | +0.23 |

TABLE 5-continued

Healing Rates of Decubitus Ulcer Wounds Treated with Recombinant Human IL-1β

| Dose | Patient | Gilman Index (cm) | | |
|---|---|---|---|---|
| | | Pre-treatment | Treatment | Post-Treatment |
| 1.0 μg | 3 | +0.14 | +0.31 | +0.24 |
| | 4 | −0.01 | +0.22 | −0.05 |
| | 5 | +0.17 | +0.46 | +0.16 |
| | 6 | −0.07 | +0.19 | −0.01 |
| 2.0 μg | 7 | −0.10 | 0.00 | +0.27 |
| | 8 | +0.18 | 0.00 | +0.17 |
| | 9 | −0.07 | +0.17 | +0.20 |
| 4.0 mg | 10 | +0.32 | +0.08 | +0.33 |
| | 11 | +0.02 | −0.06 | −0.02 |
| | 12 | +0.05 | +0.23 | −0.25 |
| 6.0 mg | 13 | −0.01 | −0.07 | (removed due to infection) |
| | 14 | +0.25 | 0.00 | +0.88 |
| | 15 | −0.03 | +0.03 | +0.01 |

Figure 5:
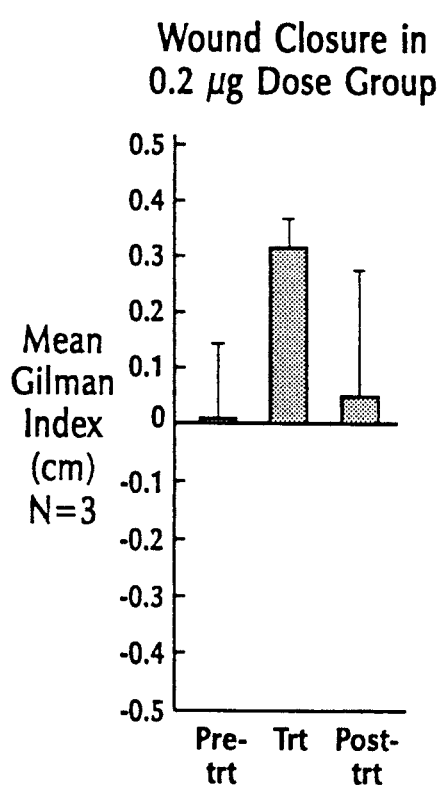
FIGS. 5-9 are graphs showing the extent of closure (Gilman Index) of decubitus ulcer wounds before, during and after being treated with 0.1 μg, 1.0 μg, 2.0 μg, 4.0 μg or 6.0 μg recombinant human IL-1β.
Figure 6:
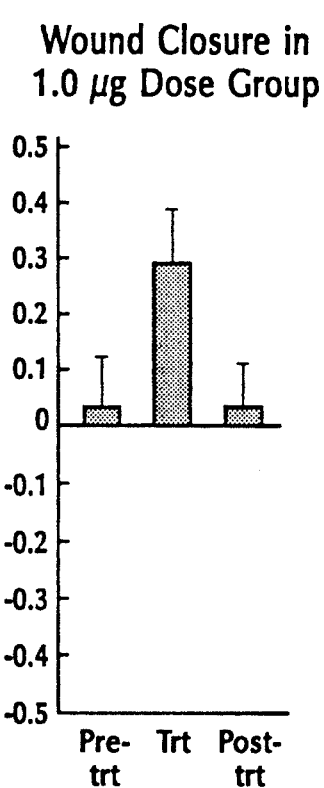
Figure 7:
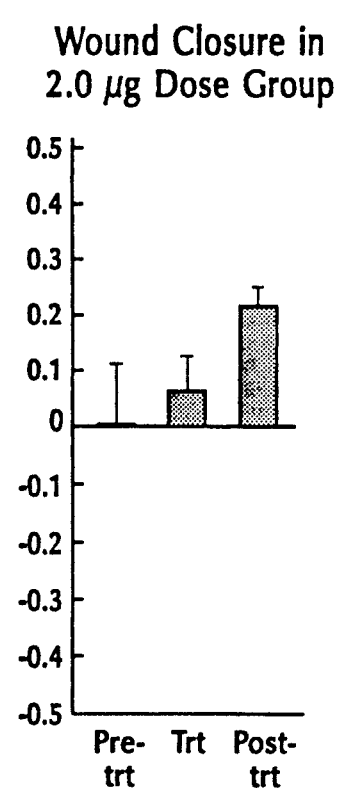
Figures 8, 9:
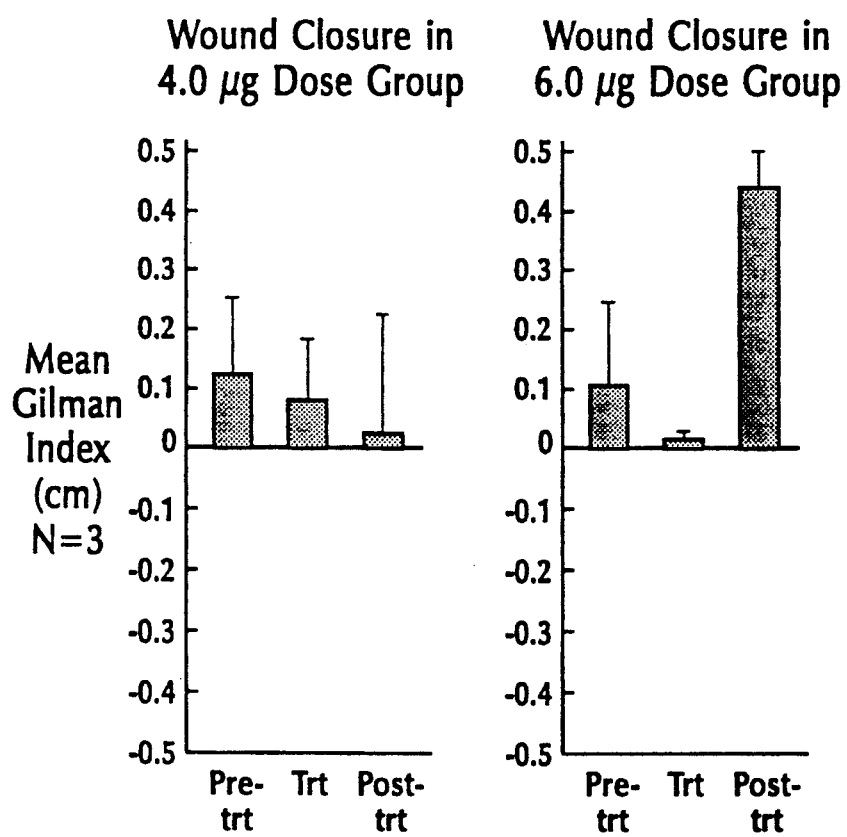

The data in Table 5 are shown graphically in FIGS. 5–9, which indicate the extent of wound closure for each group (in terms of the mean Gilman index) during pre-treatment, treatment and post-treatment with IL-1β. FIGS. 5 and 6 show that wounds heal faster during treatment with 0.2 μg and 1.0 mg of IL-1β than before or after treatment with IL-1β. FIGS. 7–9 show that wounds do not heal faster during treatment with 2.0 mg, 4.0 mg and 6.0 mg than before or after treatment with IL-1β. Individually, however, some patients (patients 9, 12 and 15), did show improved wound healing during treatment with IL-1β.

EXAMPLE 6

Effect of Topical Application of Human IL-1 on Pressure Sores in Humans Aged 51–75

A study was conducted to determine the effect of topically applied recombinant human IL-1β gel in adults aged 51–75 with stage II (skin broken through to dermis) or stage III (skin broken, invading subcutaneous tissues) decubitus ulcerations (pressure sores). The IL-1β used in this study was formulated in a recombinant human IL-1β gel, produced as described above in Example 3. A total of seven patients (divided into two groups of three patients and one group of a single patient) participated in the study. Each group received one of three dosages of recombinant human IL-1β gel (0.2, 1.0 and 2.0 μg/wound/day) applied in a 2 cc volume of gel daily to a single decubitus ulceration for a period of 14 consecutive days. The group containing only a single patient received the 2.0 μg/wound/day dosage.

The Gilman indices (see Example 5, above) for wounds treated with IL-1β gel as described above, are shown below in Table 6.

TABLE 6

Healing Rates of Decubitus Ulcer Wounds Treated with Recombinant Human IL-1β

| Dose | Patient | Gilman Index (cm) | | |
|---|---|---|---|---|
| | | Pre-treatment | Treatment | Post-Treatment |
| 0.1 μg | 1 | +0.13 | +0.10 | +0.25 |
| | 2 | +0.07 | +0.02 | (no data available) |
| | 4 | −0.02 | +0.36 | +0.07 |
| 1.0 μg | 5 | +0.15 | +0.52 | (wound healed) |
| | 6 | +0.13 | +0.28 | +0.23 |
| | 7 | +0.20 | +0.40 | +0.17 |
| 2.0 μg | 8 | −0.03 | +0.08 | 0.00 |

The data in Table 6 are shown graphically in FIGS. 10–12, which indicate the extent of would closure for each group (in terms of the mean Gilman index) during pre-treatment, treatment and post-treatment with IL-1β. FIGS. 10–12 show that wounds heal faster during treatment with 0.2 μg, 1.0 μg and 2.0 μg of IL-1β than before or after treatment with IL-1β.

EXAMPLE 7

Effect of Topical Application of Human IL-1 on Partial-Thickness Wounds in Humans A randomized, double-blind, placebo-controlled clinical study was conducted to evaluate the efficacy and safety of recombinant human IL-1β (rhu IL-1β) gel in treating surgically-created partial-thickness wounds on human patients. A total of thirty six (36) subjects participated in the study. Each patient received two surgically created wounds, one on each anterior thigh, with a dermatome using sterile surgical procedures. Each wound measured 2.0 cm×2.0 cm×0.3 mm deep. One wound on each patient was treated daily with 1 ml placebo gel. The other wound on each patient was either treated daily with 1 ml of recombinant human IL-1β gel at one of three different dose levels (0.1, 0.5 or 5.0 μg/day) or with dressing alone (to determine if the gel vehicle used had any effect on wound healing rates). The sample size for each dose (and for the dressing alone control) was nine (9) patients. Recombinant IL-1β gel was produced as described above in Example 3. After applying a Karaya plate or duoderm cut-out, an oxygen permeable occlusive Op Site ® dressing was placed on all wounds. The patients were treated until the wounds were completely healed.

The results of this clinical study are reported below in Table 7 which shows the mean and median number of days required for the wounds to fully heal. Within each dose group, the wounds were compared using paired t-tests. Dose responses were also examined by comparing across dose levels the differences in time to healing between rhu IL-1β gel and placebo gel using analysis of variance.

TABLE 7

Effect of Topical Application of Human IL-1 on Partial-Thickness Wounds in Humans

| Dose (ug/g gel) | | Time to Healing (days) | | | |
|---|---|---|---|---|---|
| | | IL-1β (or placebo) | Placebo | IL-1β or dressing minus placebo | P-value[1] |
| 0.1 | mean | 0.89 | 9.78 | 0.11 | 1.000 |
| | median | 10 | 10 | 0 | |
| 0.5 | mean | 11.0 | 12.22 | −1.22 | 0.023 |
| | median | 11 | 12 | −1 | |
| 5.0 | mean | 11.22 | 11.33 | −0.11 | 1.000 |
| | median | 11 | 11 | 0 | |
| 0 | mean | 10.56 | 11.56 | −1.00 | 0.094 |

TABLE 7-continued

Effect of Topical Application of Human IL-1 on Partial-Thickness Wounds in Humans

| Dose (ug/g gel) | | Time to Healing (days) | | | |
|---|---|---|---|---|---|
| | | IL-1β (or placebo) | Placebo | IL-1β or dressing minus placebo | P-value[1] |
| (dressing only) | median | 11 | 12 | −1 | |

[1]Wilcoxon Signed-Rank test on differences

The P-values for differences among dose responses, determined using the Kruskal-Wallis test (overall) and Wilcoxon Rank-Sum tests (pairwise), were as follows:
p=0.015 (overall),
p=0.006 (0.1 vs 0.5)
p=0.434 (0.1 vs 5.0)
p=0.053 (0.5 vs 5.0)
The above data indicate that, for the 0.5 μg dose level, there was a significant difference in healing time between placebo and IL-1β-treated wounds, thus demonstrating that IL-1β gel accelerated healing. In contrast, for the 0.1 μg, 0.5 μg and dressing only dose levels, there was no significant difference in healing time between placebo control and IL-1β treated (or dressing only) wounds.

The foregoing embodiments of the invention are meant to be illustrative only and not limiting. Obvious variants or equivalents of the compositions actually disclosed herein would include various wound healing compositions comprising mutant or analog forms of IL-1 proteins having similar biological activities, or wound healing compositions for veterinary use comprising appropriate quantities of IL-1 proteins of particular species, for example, bovine, porcine, equine, ovine, canine, or feline IL-1 proteins. In addition, dosages will vary depending on the depth or type of wound and on whether the individual being treated is normal or impaired. All such variants are considered to be within the scope of the following claims.

What is claimed is:

1. A method for promoting wound healing in a mammal, comprising the step of contacting a wound site with interleukin-1 (IL-1) formulated in a physiologically acceptable hydrophilic vehicle in an amount effective to promote wound healing.

2. A method for promoting wound healing in a mammal according to claim 1, wherein the IL-1 is applied to a wound site in an amount of from about 0.01 μg to about 10 μg IL-1 per ml of a physiologically acceptable hydrophilic vehicle per day.

3. A method for promoting wound healing in a mammal according to claim 1, wherein the IL-1 is applied to a wound site in an amount of from about 0.1 μg to about 5 μg IL-1 per ml of a physiologically acceptable hydrophilic vehicle per day.

4. A method for promoting wound healing in a mammal according to claim 1, wherein the IL-1 is applied to a wound site in an amount of from about 0.2 μg to about 1 μg IL-1 per ml of a physiologically acceptable hydrophilic vehicle per day.

5. A method for promoting wound healing in a mammal according to claim 1, wherein the IL-1 is applied to a wound site in an amount of about 0.5 μg IL-1 per ml of a physiologically acceptable hydrophilic vehicle per day.

6. A method for promoting wound healing in a mammal according to claim 1, wherein the IL-1 is applied to a wound site to provide a dose of from about 0.01 μg to about 3 μg IL-1 per cm² of wound surface area per day.

7. A method for promoting wound healing in a mammal according to claim 1, wherein the IL-1 is applied to a wound site to provide a dose of from about 0.1 μg to about 0.5 μg IL-1 per cm² of wound surface area per day.

8. A method for promoting wound healing in a mammal according to claim 1, wherein the wound is a chronic bedsore.

* * * * *

UNITED STATES PATENT AND TRADEMARK OFFICE
CERTIFICATE OF CORRECTION

PATENT NO. : 5,202,118  Page 1 of 2
DATED : April 13, 1993
INVENTOR(S) : Steven Gillis and Cindy A. Jacobs It is certified that error appears in the above-identified patent and that said Letters Patent is hereby corrected as shown below:

Column 1, line 63, "426" should be --462--.
Column 2, line 16, "cDNA" should be --cDNAs--.
           line 50, "does" should be --dose--.
           line 58, "defore" should be --before--.
           line 59, "after treated" should be --after being treated--.
Column 4, line 55, "metyl" should be --methyl--.
Column 5, line 36, "pKK2233" should be --pKK223-3--.
           line 52, "AluI and EcoRI" should be --AluI and EcoRI--.
           line 55, "EcoRI and NdeI" should be --EcoRI and NdeI--.
Column 6, line 10, "BamHI/EcoRI" should be -- BamHI/EcoRI--.
           line 11, "Sau3A/EcoRI" should be --Sau3A/EcoRI--.
           line 13, "EcoRI and PstI" should be --EcoRI and PstI--.
           line 18, "EcoRI/HpaI" should be --EcoRI/HpaI--;
           "      "synthesis" should be --synthetic--.
Column 8, line 52, "4" should be --(4)--.
Column 12, line 23, "glycal" should be --glycol--.
Column 14, line 37, "was" should be --were--.
           line 47, "was" should be --were--.
           TABLE 3, on second line "Wound Healing" should follow "Epidermal" on first line;
           "      on second line "Days After Wounding" should be centered.

UNITED STATES PATENT AND TRADEMARK OFFICE
CERTIFICATE OF CORRECTION

PATENT NO. : 5,202,118

DATED : April 13, 1993

INVENTOR(S) : Steven Gillis and Cindy A. Jacobs

It is certified that error appears in the above-identified patent and that said Letters Patent is hereby corrected as shown below:

Column 15, TABLE 4, asterisk footnote should read:

$$-\!-\!*\frac{(HT_{50} \text{ Control} - HT_{50} \text{ Treatment}) \times 100}{(HT_{50} \text{ Control})}-\!-$$

Column 16, line 42, "1.0 mg" should read --1.0 µg--.

Column 17, line 17, "would" should read --wound--.

Signed and Sealed this

Thirteenth Day of September, 1994

Attest:

BRUCE LEHMAN

Attesting Officer     Commissioner of Patents and Trademarks